United States Patent [19]

Elsheikh

[11] Patent Number: 5,811,603
[45] Date of Patent: Sep. 22, 1998

[54] GAS PHASE FLUORINATION OF 1230ZA

[75] Inventor: Maher Y. Elsheikh, Wayne, Pa.

[73] Assignee: Elf Atochem North America, Inc., Philadelphia, Pa.

[21] Appl. No.: 980,746

[22] Filed: Dec. 1, 1997

[51] Int. Cl.$^6$ .................................................. C07C 17/08
[52] U.S. Cl. .......................................... 570/166; 570/169
[58] Field of Search ...................................... 570/166, 169

[56] References Cited

U.S. PATENT DOCUMENTS 5,171,901  12/1992  Gassen et al. .......................... 570/169
5,616,819  4/1997  Boyce et al. ............................ 570/167

*Primary Examiner*—Alan Siegel
*Attorney, Agent, or Firm*—Stanley A. Marcus; William D. Mitchell

[57] ABSTRACT

A process for the fluorination of 1230za is provided, wherein 1230za is contacted with HF in the gas phase in the presence of an aluminum fluoride or chromium-based fluorination catalyst under conditions sufficient to produce a reaction mixture containing 1233zd, 1234ze and 245fa. 245fa is a known foam blowing agent and refrigerant, while 1233zd and 1234ze are known intermediates useful for preparing 245fa.

2 Claims, No Drawings

GAS PHASE FLUORINATION OF 1230ZA

BACKGROUND OF THE INVENTION

This invention relates to the gas phase catalyzed fluorination of 1, 1,3,3-tetrachloro-2-propene (1230za), particularly to processes wherein said 1230za is contacted with hydrogen fluoride (for convenience hereafter referred to as "HF") in the gas phase with an aluminum fluoride or chromium catalyst to prepare the desired fluorination products $CF_3CH=CHCl$ (1,1,1-trifluoro-3-chloro-2-propene or "1233zd"), $CF_3CH=CHF$ (1,1,1,3-tetrafluoro-2-propene or "1234ze"), $CF_3CH_2CHF_2$ (1,1,1,3,3 -pentafluoropropane or "245 fa") and mixtures thereof. 245fa is known to have utility as a foam blowing agent and refrigerant, while 1233zd and 1234ze are known intermediates for producing 245fa, as taught, for example in U.S. Pat. 5,616,819 and in copending application Docket No. IR3514 filed on even date herewith. U.S. Pat. 5,616,819 discloses that previous attempts to fluorinate 1230za in a catalyzed reaction, such as with $SbCl_5$, $SnCl_4$ and $HOSO_3F$, primarily lead to the formation of oligomeric products (109g of oligomeric material and 3g of 1233zd in Example 1(ii) thereof). It is thus an object of this invention to provide a catalyzed fluorination process for successfully converting 1230za to useful fluorination products.

BRIEF SUMMARY OF THE INVENTION

A process for preparing fluorination products of the formula $CF_3R$, where R is selected from $—CH=CHCl$, $—CH=CHF$, $—CH_2CHF_2$ and mixtures thereof, is provided, which process comprises (a) contacting 1230za with HF in the gas phase in the presence of an aluminum fluoride or chromium fluorination catalyst (preferably an activated chromium oxide catalyst) under conditions sufficient to produce a reaction mixture containing the desired fluorination products and (b) separating the desired fluorination products from said reaction mixture. Total (100%) conversion of the 1230za has been found to occur, so that the reaction mixture primarily contains the desired fluorination products (1233zd, 1234ze, and 245fa), hydrogen chloride (HCl) by-product, and unreacted HF.

Various means can be used to obtain or generate 245fa from this (original) reaction mixture. For example, the HCl may be removed by conventional means known in the art (such as absorption or distillation), following which the reaction mixture (less the HCl) may be fluorinated again to increase the amount of 1234ze intermediate, which 1234ze is then separated and converted to 245fa, all as taught in said copending application (Docket No. 3514). Alternatively, the 245fa, 1233zd and HF can be separated from the original fluorination reaction mixture and recycled to the reactor, such as by distillation to separate the original reaction mixture into streams containing (i) the 245fa, 1233zd and HF and (ii) 1234ze and HCl. The 1234ze and HCl in the second stream (ii) can then be separated by the aforesaid conventional methods, with the separated 1234ze then being converted to 245fa as taught in said copending application (Docket No. 3514). Or, finally, the 245fa may be recovered directly from the original reaction mixture, such as via distillation.

Separation of HF from 245fa/HF mixtures is taught, for example, in world patent application WO97/27163.

DETAILED DESCRIPTION

It has now been discovered that aluminum fluoride and chromium-based fluorination catalysts are useful for successfully fluorinating 1230za in a catalyzed, gas phase process to produce the desired products, 1233zd, 1234ze, 245fa and mixtures thereof, total conversion of the 1230za having been found to be attainable.

The 1230za starting material can be prepared by the pyrolysis of 1,1,1,3,3pentachloropropane (240fa), such as illustrated in the examples hereinbelow.

The 1230za fluorination process involves contacting 1230za with HF in a first reaction zone in the gas phase in the presence of the aluminum fluoride or chromium based fluorination catalyst under conditions sufficient to convert the 1230za to fluorination products comprising 1233zd, 1234ze and 245fa. Thus, the reaction mixture primarily contains 1233zd, 1234ze, 245fa, HF and HCl. The HF:1230za molar ratio is typically from about 5:1 to 50:1, but is preferably from about 5:1 to about 20: 1. Temperatures of from about 30° C. to about 400° C. are typically used, preferably from about 100° C. to about 350° C. Pressures are typically from about 0 to about 400 psig, preferably from about 120–200 psig. A variety of chromium based catalysts can be used, such as chromium oxide, $Cr_2O_3$, which chromium-based catalyst is either unsupported or supported on fluorided alumina or activated carbon, the chromium catalyst being used alone or in the presence of a co-catalyst such as an alkali metal (for example, sodium, potassium or lithium), alkaline earth metal (for example, calcium, barium or magnesium), zinc, manganese, cobalt or nickel. Two such preferred chromium catalysts are chromium oxide and chromium/nickel on fluorided alumina, preparation of this latter catalyst being taught, for example, in European Patent 486333. The chromium-based catalysts are preferably activated before use, typically by a procedure wherein the catalyst bed is heated to about 370–380° C. (normally with a continuous flow of nitrogen), after which a mixture of approximately equal volumes of HF and air or nitrogen (preferably nitrogen) are fed over the catalyst bed for about 18 hours. The preferred chromium oxide catalyst has a high surface area, such as from about 20 to about 250 square meters per gram. An oxygen or chlorine cofeed can also be used to extend the catalyst lifetime, typically in an amount of from about 0.005 to about 0.20 moles of chlorine or oxygen per mole of organic in the feed, the oxygen being introduced as an oxygen-containing gas such as air, oxygen, or an oxygen/nitrogen mixture. Contact times (catalyst volume divided by the total flow rate of reactants and cofeeds) are typically from about 1 to about 250 seconds, more typically from about 1 to about 120 seconds.

The 245fa may be recovered directly from the first reaction zone mixture by methods known in the art, such as distillation. Or, following the teachings of said copending application (Docket No. IR 3514), the 1234ze produced in the first reaction zone can be separated from the reaction mixture and then contacted with HF in a second reaction zone under conditions sufficient to produce 245fa. One manner of carrying out this separation is to subject the reaction mixture from the first reaction zone to two distillations, the first distillation serving to separate the lower boiling 1234ze and HCl (taken off at top of the column) from the 245fa, 1233zd, HF and any other heavies (taken off at the bottom of the column), with the second distillation serving to separate the lower boiling HCl (removed at top of column) from the 1234ze (removed at column bottom and fed to second reaction zone). Preferably, the bottoms from the first column are then recycled to the first reaction zone, where the 1233zd and 245fa can be reacted to produce 1234ze. The fluorination of 1234ze to 245fa in the second reaction zone can be carried out using a catalyzed gas phase, liquid phase, or mixed phase system as taught in said copending application (Docket No. IR3514) to produce a mixture whose major components are 245fa, 1234ze and HF. The 245fa (boiling point 15° C.) can then be recovered from the reaction mixture by conventional techniques, such as distillation, the lower boiling 1234ze (boiling point -16° C.) and any HF/245fa azeotrope coming off overhead, where it can be recycled to the reactor. Alternatively, the HCl may be removed from the first reaction zone mixture by methods known in the art such as by absorption (in water or caustic solution) or distillation, following which the reaction mixture (less the HCl) may be fluorinated again to increase the amount of 1234ze, which 1234ze is then separated and converted to 245fa as aforesaid.

The practice of the invention is illustrated in more detail in the following non-limiting examples using unsupported high surface area chromium oxide catalysts (surface area in the range of about 20–200 m$^2$/g):

Catalyst (Cr$_2$O$_3$) was activated at 380° C. by cofeeding a mixture of HF (30 cc/min) and nitrogen (30 cc/min) for 18 hours. 1230za and HF, in varying molar ratios ("m.r." s), were then fed to the reactor, together with any cofeed of air (Examples 1 and 2 only), over the activated catalyst under the conditions, and with the results, set forth below, 100% conversion of the 1230za being achieved in all cases:

| Example # | 1 | 2 | 3 | 4 | 5 |
|---|---|---|---|---|---|
| Temperature (°C.) | 330 | 330 | 150 | 175 | 200 |
| Pressure (psig) | 165 | 165 | 0 | 0 | 0 |
| HF:1230za (m.r.) | 10 | 20 | 10 | 10 | 10 |
| Contact time (seconds) | 53 | 28 | 8 | 8 | 7 |
| Moles of oxygen in air cofeed per mole of 1230za | 0.03 | 0.03 | — | — | — |
| Selectivity for 1233zd (%) | 80.8 | 66.6 | 93.9 | 65.8 | 53.1 |
| Selectivity for 1234ze (%) | 6.8 | 11.5 | 0.5 | 0.5 | 1.3 |
| Selectivity for 245fa (%) | 10.5 | 20.7 | 1.1 | 27.7 | 42.5 |

1230za starting material was conveniently prepared in three runs by heating 240fa at 100° C., 150° C. and 200° C., respectively, in the presence of activated Cr$_2$O$_3$ catalyst. In all runs greater than 99% conversion was achieved, with greater than 93% selectivity for 1230za.

I claim:

1. A process for preparing fluorination products of the formula CF$_3$R, where R is selected from —CH=CHCl, —CH=CHF, —CH$_2$CHF$_2$ and mixtures thereof, which process comprises (a) contacting 1,1,3,3-tetrachloro-2-propene with hydrogen fluoride in the gas phase with an aluminum fluoride or chromium fluorination catalyst under conditions sufficient to produce a reaction mixture containing the desired fluorination products and (b) separating the desired fluorination products from said reaction mixture.

2. A process as in claim 1 wherein the fluorination catalyst is an activated chromium oxide catalyst.

* * * * *